United States Patent [19]

Lipson

[11] Patent Number: 5,779,699

[45] Date of Patent: *Jul. 14, 1998

[54] SLIP RESISTANT FIELD FOCUSING ABLATION CATHETER ELECTRODE

[75] Inventor: David Lipson, Shoreview, Minn.

[73] Assignee: Medtronic, Inc., Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 626,750

[22] Filed: Mar. 29, 1996

[51] Int. Cl.$^6$ .................................................. A61N 1/00
[52] U.S. Cl. .......................... 606/41; 606/45; 606/49; 607/122
[58] Field of Search ........................... 128/639, 642, 128/702; 606/28, 29, 41, 45, 46, 49; 607/122; 600/372–386, 392–397, 515

[56] References Cited

U.S. PATENT DOCUMENTS

| | | |
|---|---|---|
| 3,470,876 | 10/1969 | Barchilon . |
| 3,605,725 | 9/1971 | Bentov . |
| 4,502,492 | 3/1985 | Bornzin . |
| 4,601,294 | 7/1986 | Danby et al. ............. 128/642 |
| 4,685,457 | 8/1987 | Donenfeld . |
| 4,753,223 | 6/1988 | Bremer . |
| 4,826,087 | 5/1989 | Chinery . |
| 4,832,048 | 5/1989 | Cohen . |
| 4,838,859 | 6/1989 | Strassmann . |
| 4,848,352 | 7/1989 | Pohndorf et al. ............. 128/642 |
| 4,860,943 | 8/1989 | Cooper . |
| 4,944,727 | 7/1990 | McCoy . |
| 4,960,134 | 10/1990 | Webster, Jr. ............. 128/642 |
| 5,103,804 | 4/1992 | Abele . |
| 5,275,162 | 1/1994 | Edwards . |
| 5,281,213 | 1/1994 | Milder . |
| 5,281,217 | 1/1994 | Edwards . |
| 5,281,218 | 1/1994 | Imran . |
| 5,318,525 | 6/1994 | West . |
| 5,555,618 | 9/1996 | Winkler ............. 128/642 X |

OTHER PUBLICATIONS

Langberg et al., "Temperature-GuidedRadiofrequency Catheter Ablation with very Large Distal Electrodes", *Circulation*, vol. 88, No. 1, Jul., 1993 pp. 245–249.

Langberg et al., "Radiofrequency Catheter Ablation: The Effect of Electrode Size on Lesion Volume in Vivo", *Pace*, Oct. 1990, vol. 13, pp. 1242–1248.

Haines et al., "Electrode Radius Predicts Lesion Radius During Radiofrequency Energy Heating", *Thermodynamic Model Of RadioFrequency Heating*, pp. 125–129.

*Primary Examiner*—Jennifer Bahr
*Assistant Examiner*—Stephen Huane
*Attorney, Agent, or Firm*—Reed A. Duthler; Harold R. Patton

[57] ABSTRACT

An RF ablation catheter of the type comprising a flexible elongate catheter body having at least one lumen therethrough and having a proximal handle end and a distal end section adapted to be introduced into a heart chamber, at least one electrical conductor extending from the handle to the distal tip section within the at least one lumen for conduction RF energy, and a distal tip electrode coupled to the distal end section of the catheter body and electrically coupled with the at least one electrical conductor. The distal tip electrode is formed with a slip resistant, field focusing exterior contour for maintaining a position of the distal tip electrode bearing against the endocardium of the patient's heart, without penetrating the myocardium thereof, achieved through manipulation of the catheter distal tip section, and focusing ablation energy into the endocardium. The distal tip electrode is formed of a generally cylindrical, electrically conductive, electrode body having a hemispheric end and a tubular side wall at the distal end of the catheter body, and the exterior contour providing means further comprises a plurality of depressions formed by bores or annular or spiral or longitudinally elongated grooves formed in the hemispheric end and/or side wall. The exterior contour additionally assists in cooling the distal tip electrode.

8 Claims, 4 Drawing Sheets

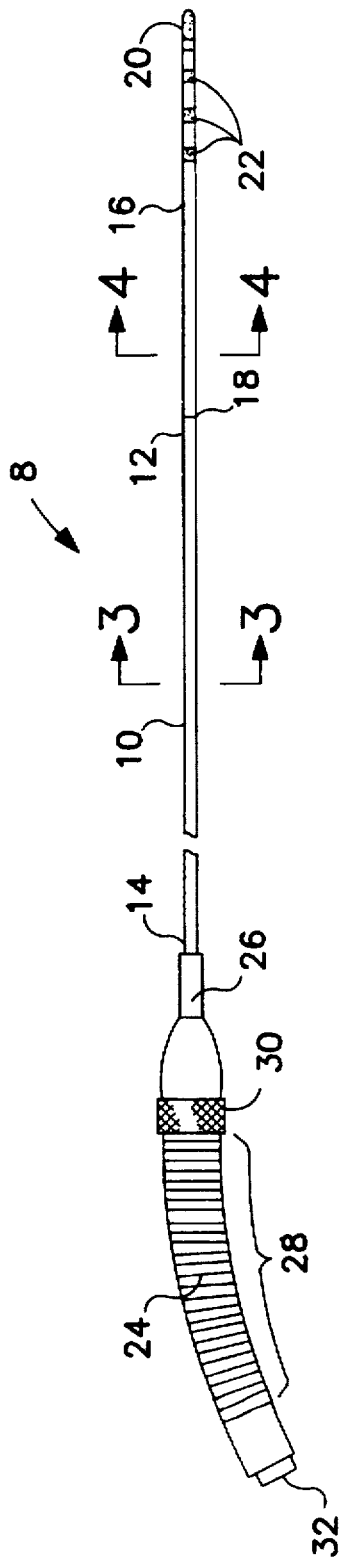
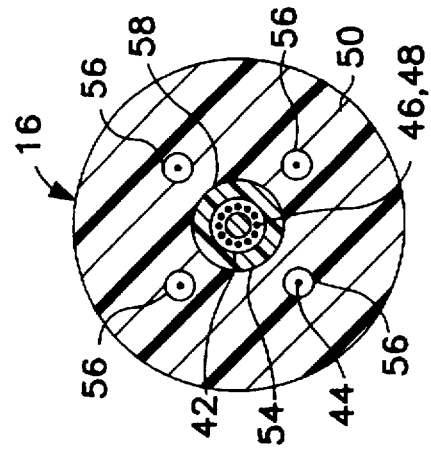
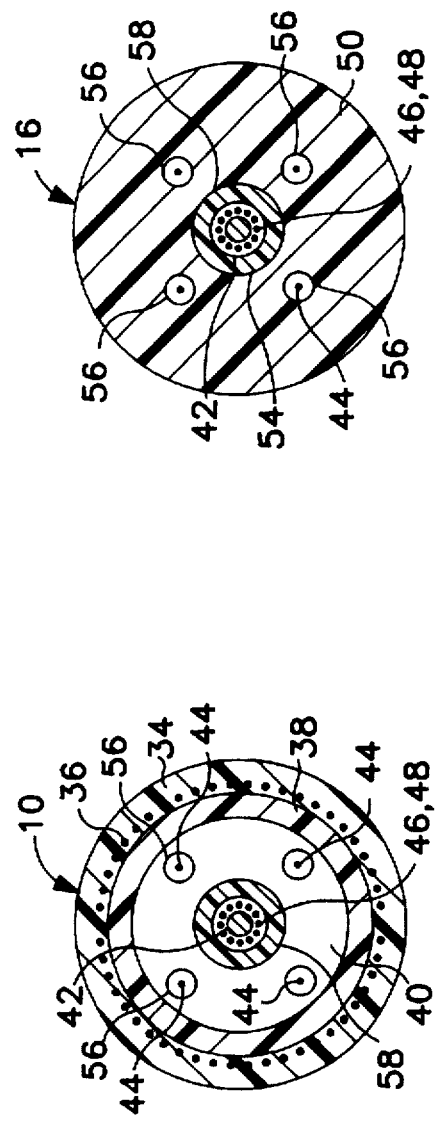

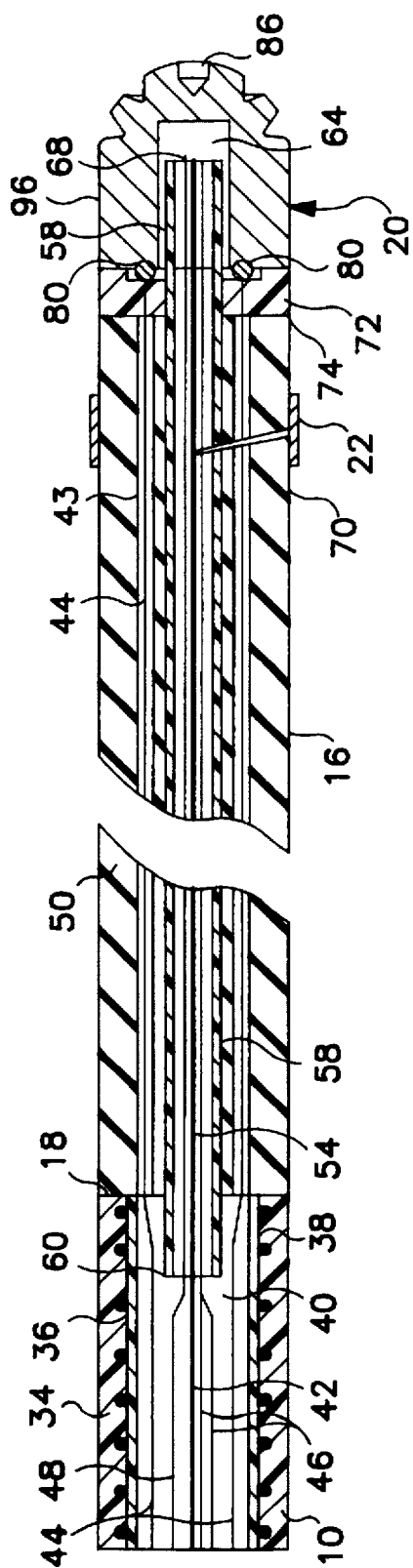
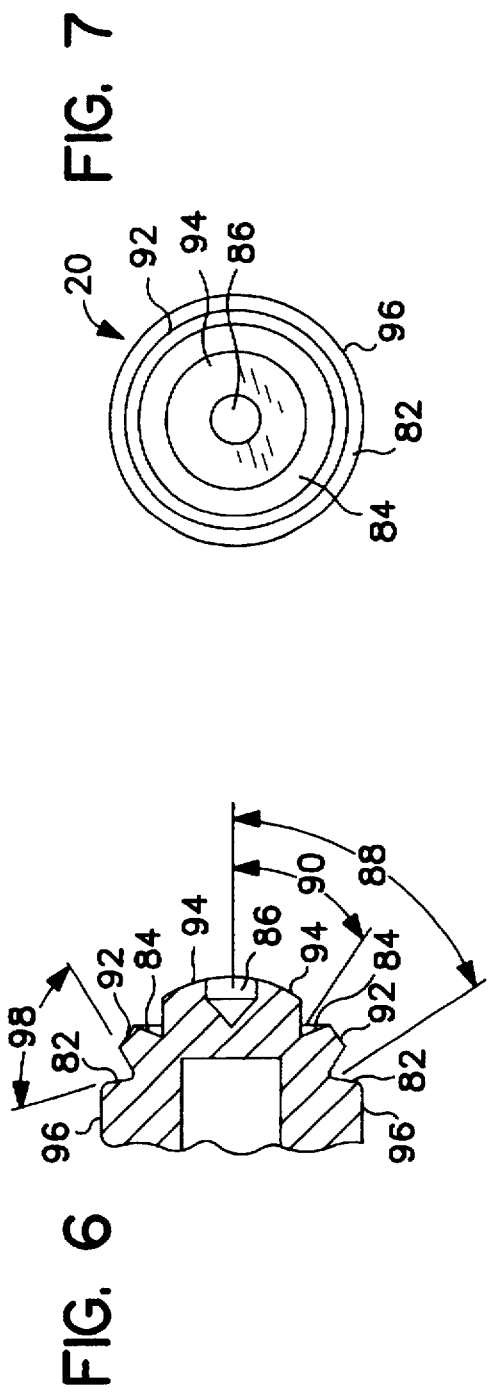
FIG. 5
FIG. 6
FIG. 7

SLIP RESISTANT FIELD FOCUSING ABLATION CATHETER ELECTRODE

FIELD OF THE INVENTION

The present invention relates generally to the field of electrophysiology and more particularly to an improved slip resistant, field focusing, ablation catheter electrode.

BACKGROUND OF THE INVENTION

Symptoms of abnormal heart rhythm are generally referred to as cardiac arrhythmias, with an abnormally slow rhythm being classified as a bradycardia and an abnormally rapid rhythm being referred to as a tachycardia. The present invention is concerned with the treatment of tachycardias which are frequently caused by be presence of an "arrhythmogenic site" or "accessory atrioventricular pathway" close to the inner surface of one of the chambers of the heart. The heart includes a number of normal pathways which are responsible for the propagation of signals necessary for normal electrical and mechanical function. The presence of arrhythmogenic sites or accessory pathways can bypass or short circuit the normal pathways, potentially resulting in very rapid heart contractions, referred to as tachycardias. Tachycardias may be defined as ventricular tachycardias (VT's) and supraventricular tachycardias (SVT's). VT's originate in the left or right ventricle and are typically caused by arrhythmogenic sites associated with a prior myocardial infarction. SVT's originate in the atria and are typically caused by an accessory pathway.

Treatment of both ventricular and supraventricular tachycardias may be accomplished by a variety of approaches, including drugs, surgery, implantable pacemakers/defibrillators, and catheter ablation of the pathway. While drugs may be the treatment or choice for many patients, they only mask the symptoms and do not cure the underlying cause. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. The catheter-based treatments rely on the application of various destructive energy sources to the target tissue, including direct current electrical energy, radio frequency electrical energy, laser energy, and the like. Of particular interest to the present invention are radiofrequency (RF) ablation protocols which have proven to be highly effective in tachycardia treatment while exposing the patient to minimum side effects and risks. Radiofrequency catheter ablation is generally performed after an initial mapping procedure where the locations of the arrhythmogenic sites and accessory pathways are determined. After mapping, a catheter having a suitable electrode is introduced to the appropriate heart chamber and manipulated so that the electrode lies proximate the target tissue. Radiofrequency energy is then applied through the electrode to the cardiac tissue in order to ablate a region of the tissue which forms part of arrhythmogenic site or the accessory pathway. By successfully destroying that tissue, the abnormal signaling patterns responsible for the tachycardia cannot be sustained. A method and system for performing RF ablation by controlling temperature at the ablation site is described in co-pending application Ser. No. 966,683, filed Apr. 10, 1992, entitled "Method and System for Radiofrequency Ablation of Cardiac Tissue", hereby incorporated herein by reference.

Catheters utilized in RF ablation are inserted into a major vein or artery, usually in the neck or groin area, and guided into the chambers of the heart by appropriate manipulation through the vein or artery. The tip of the catheter must be manipulatable by the user from the proximal end of the catheter, so that the distal electrode can be positioned against the tissue region to be ablated. The catheter must have a great deal of flexibility in order to follow the pathway of the major blood vessels into the heart, and the catheter must permit user manipulation of the tip even when the catheter is in a curved and twisted configuration. Because of the high degree of precision required for proper positioning of the tip electrode, the catheter must be manipulatable with a high degree of sensitivity and controllability. In addition, the distal portion of the catheter must be sufficiently resilient in order to be positioned against the wall or the ventricle and maintained in a position during ablation without being displaced by the movement of the beating heart. Along with the steerability, flexibility and resiliency, the catheter must have a sufficient degree of torsional stiffness to permit user manipulation from the proximal end.

Steerable catheters are known for use in a variety of medical procedures. See, for example, U.S. Pat. Nos. 4,998,916 to Hammerslag, 4,944,727 to McCoy, 4,838,859 to Strassmann, 4,826,087 to Chinery, 4,753,223 to Bremer, 4,685,457 to Donenfeld, 3,605,725 to Bentov, 3,470,876 to Barchilon and 4,960,134 to Webster, Jr. Typically, such catheters employ a plurality of steering wires, usually three, or four, extending from a steering mechanism at the proximal end of the catheter to an anchor point at the distal end of the catheter. By tensioning certain of the steering wires using the control mechanism, the tip of the catheter can be manipulated in a desired direction. In addition to being steerable in the lateral direction, further positioning of known catheters is accomplished by rotating the catheter as a whole about its longitudinal axis, typically by turning or twisting the proximal end of the catheter. This exerts a torque along the length of the catheter which is translated into a rotational motion at the distal end, allowing a laterally deflected distal tip to be rotated.

An improvement of such steerable RF ablation catheters is disclosed in commonly assigned, U.S. Pat. No. 5,318,525 to West et al. and generally depicted in FIG. 1. A shaped handle 24 is coupled to pull wires within the catheter body 10 for deflecting the distal section 16 of the catheter body 10 into a curve to facilitate rough positioning of the RF ablation tip electrode 20 at a site in the ventricle 140 of a patient's heart. As depicted in FIG. 1, the distal tip electrode 20 has been advanced through a percutaneous introduction into a vein and transvenously advanced into the right ventricle 140. The distal section 16 in the right ventricle 140 s formed into the curve by manipulation or shaping of the handle 24, and rough positioning is achieved by rotating the entire handle 24 and catheter body 10 to aim the tip electrode at the site to be ablated. Fine positioning at the site is obtained while rotating torque ring 30 as described in the '525 patent. The advancement and rotation of the catheter body 10 is accomplished with the assistance of fluoroscopy. Fine positioning in relation to a specific conduction pathway site is monitored by monitoring electrical signals from the site conducted up the electrical conductors within the lead body 10 and determining by mapping that the conduction pathway exhibits an electrogram earlier in time than adjacent heart tissue. When the electrode tip 20 is located at the desired site, RF energy is applied from a source through the connector 32 and to the conductors to within catheter body 10 to the tip electrode 20.

In this procedure, it is important that the tip electrode remain positioned at the exact site and not slip during the delivery of the RF ablation energy. If the tip electrode slips in use, then the RF energy damages conduction pathways that are needed for intrinsic sinus heart rhythm to be maintained or otherwise inappropriately interrupt desired conduction pathways or damages other heart tissue.

The typical hemispheric tip electrode is intended to bear against the endocardium while it is being used in the ablation procedure to create a lesion at some depth in the myocardium depending on the applied RF energy level. The typical tip electrode is replaced by a needle shaped, tip electrode in U.S. Pat. No. 5,281,218 to Imran. It is stated that the needle shaped tip electrode can be extended into relatively thick regions of the myocardium in order to create a lesion that, it is postulated, is deeper than can be effected using the convention electrode position bearing against the endocardium. While slippage may be eliminated, it is secondary to attaining the depth penetration into the myocardium. The depth penetration has to be carefully monitored as the needle tip could pass through a thin septum. The needle shaped, penetrating electrode increases current density and localized heating of adjacent blood and tissue and can lead to welding of the tip electrode within the penetrated tissue, making removal difficult. With high current density, the temperature rapidly rises, leading to boiling and coagulation of the blood and charring of tissue unless it is rapidly terminated. As a result, only small lesions are practically possible, and this form of electrode has not gained favor.

The concerns of blood coagulation and tissue charring also apply to the typical RF ablation catheter tips. In order to limit blood coagulation and charring of the tissue, temperature or impedance monitoring systems have been devised to monitor temperature at the tip electrode or the tissue/electrode interface impedance and to shut down the RF energy source when local temperature of the tip electrode exceeds a temperature threshold or when the tissue/electrode impedance increases above an impedance threshold. The impedance rapidly increases as with the formation of a layer of coagulated blood ("coagulum") over the exposed electrode surface. Temperature hot spots also develop in the tissue under the electrode at the point of connection to the insulating catheter body. These hot spots at the tip electrode can cause uneven heating of the tissue by the ablation energy. While the impedance or temperature monitoring system can react by shutting down the RF energy, the procedure may then be ineffective to provide a lesion of sufficient size or depth.

SUMMARY OF THE INVENTION

Accordingly, it is an object of the present invention to overcome the problems of slippage of the tip electrode of an RF ablation catheter.

It is a further object of the present invention to provide an enhanced RF field focusing pattern in a tip electrode of an RF ablation catheter and to reduce localized temperature increases leading to blood coagulation or tissue charring.

These and other objects of the invention are realized in an RF ablation catheter of the type comprising a flexible elongate catheter body having at least one lumen therethrough and having a proximal handle end and a distal end section adapted to be introduced into a heart chamber, at least one electrical conductor extending from the handle to the distal tip section within the at least one lumen for conduction RF energy, and a distal tip electrode coupled to the distal end section of the catheter body and electrically coupled with the at least one electrical conductor, the distal tip electrode having means providing a slip resistant, field focusing exterior contour for maintaining a position of the distal tip electrode bearing against the endocardium of the patient's heart, without penetrating the myocardium thereof, achieved through manipulation of the catheter distal tip section.

In particular, it is envisaged that the slip resistant and field focusing exterior contour may constitute grooves, dimples or other irregularities or depressions in the tip electrode surface arranged in a pattern to alleviate slippage and/or to increase surface area to thereby reduce temperature hot spots and concentrate current flow axially into the adjacent conduction pathway to be ablated.

In a first preferred embodiment, the distal tip electrode is formed of a generally cylindrical, electrically conductive, electrode body having a hemispheric end and a tubular side wall at the distal end of the catheter body, and the exterior contour further comprises an axially disposed bore or depression in the hemispheric end, and a plurality of annular grooves formed in the hemispheric end between the axially disposed bore and the side wall and surrounding the axially disposed bore forming the hemispheric end into a plurality of annular ridges surrounding the axially disposed bore.

In a second preferred embodiment, the distal tip electrode is formed of a generally cylindrical, electrically conductive, electrode body having a hemispheric end and a tubular side wall at the distal end of the catheter body, and the exterior contour providing means further comprises one or more spiral grooves formed in the hemispheric end and extending proximally along the side wall, with or without an axially disposed bore.

In a third preferred embodiment, the exterior contour may comprise one or more longitudinal or particularly shaped grooves extending along the side wall of the distal tip electrode.

The present invention is expected to advantageously reduce the incidence of slippage of the RF distal tip electrode and to concentrate the RF energy in delivery pathways extending distally and axially of the distal tip electrode deep into the myocardium. The redirection of energy is advantageously in an electrode/tissue interface region that is typically relatively low in the typical hemispheric ablation catheter tip electrode.

Moreover, the ridges provided by the exterior contour are expected to provide enhanced heat exchange with blood flowing past the electrode as the heart beats and more effective cooling of the tip electrode, thereby reducing formation of coagulum.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 2 is a front elevation view of a steerable catheter of a preferred embodiment of the invention having a slip resistant, field focusing, distal tip electrode;

FIG. 3 is a cross-section view of the catheter body taken along lines 3–3 of FIG. 2; FIG. 4 is a cross-section view of the catheter body taken along lines 4–4 of FIG. 2;

FIG. 5 is an enlarged, side cross-section view of the catheter body and distal tip electrode shaped in accordance with a first preferred embodiment of the invention;

FIG. 6 is a detail of FIG. 5 illustrating the cutaway facet angles of the tip electrode;

FIG. 7 is an end view of the tip electrode of the first embodiment of FIGS. 2, 5 and 6;

FIG. 9 is an enlarged, side cross-section view of the catheter body and distal tip electrode shaped in accordance with a third preferred embodiment of the invention; and .

DETAILED DESCRIPTION OF THE PREFERRED EMBODIMENTS

Figure 1:
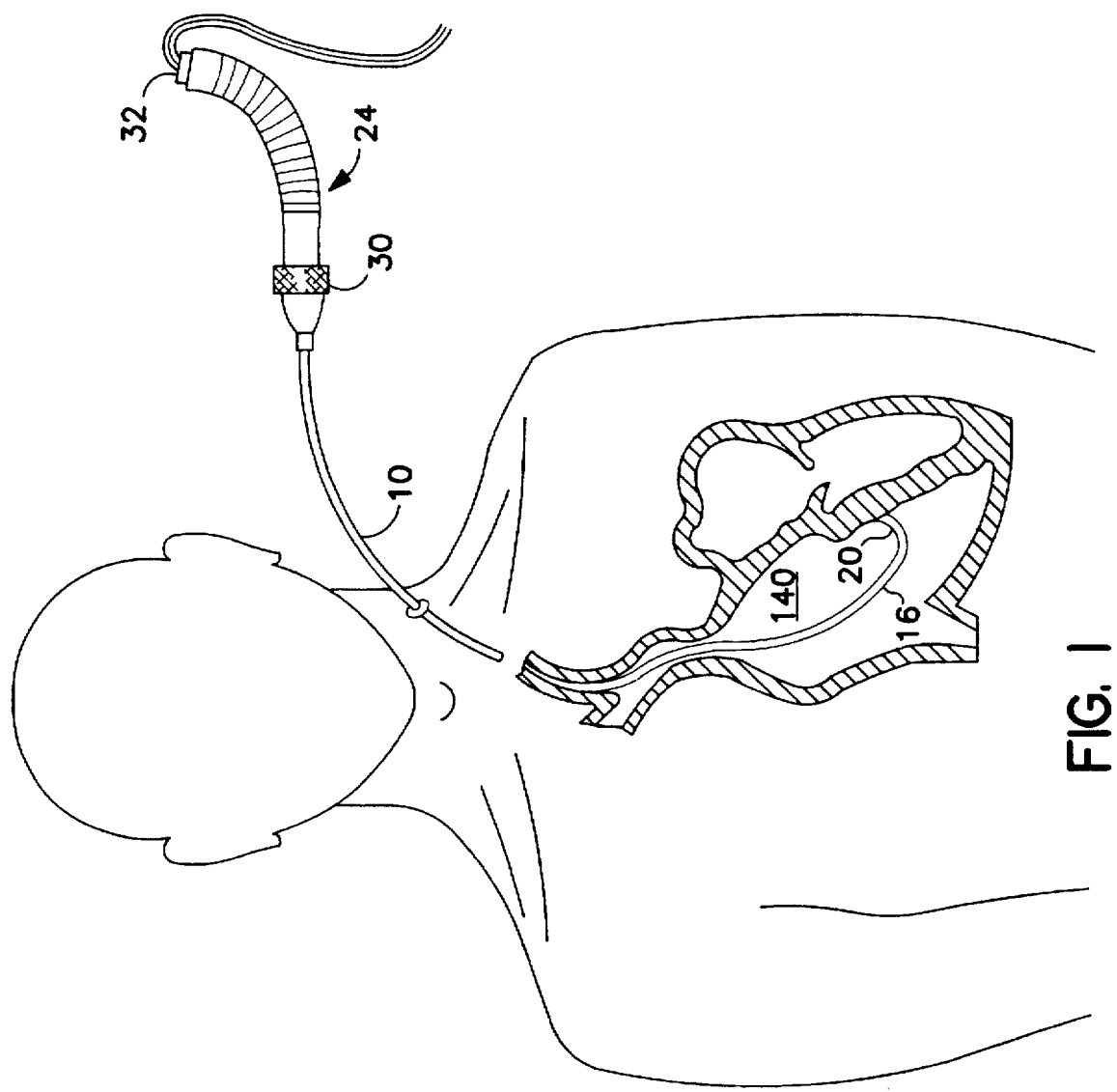
FIG. 1 is a schematic illustration of the positioning of a steerable catheter into the heart of the patient.

The present invention is embodied in a steerable catheter of the type described in the above-referenced '525 patent, incorporated herein by reference. However, it will be understood that the slip resistant, field focusing, ablation electrode may be implemented in any ablation catheter of any type in substitution for the smooth rounded or conical tip electrodes commonly used.

Referring to FIG. 2, a steerable catheter 8 constructed in accordance with the principles of the present invention comprises a shaft 10 having a distal end 12 and proximal end 14. A tip section 16 is fused at butt joint 18 to distal end 12 of shaft 10.

A tip electrode 20 is mounted at the distal end of tip section 16, with band electrodes 22 disposed on tip section 16 proximal of tip electrode 20. A thermocouple (not shown) is located in the distal end of the tip section 16 and in thermal contact with the tip electrode 20. Proximal end 14 of shaft 10 is mounted to handle 24 through strain relief 26. Handle 24 includes a shapable body 28 in a middle portion thereof. A torque ring 30 is disposed about handle 24 distally of shapable body 28, as shown in FIG. 2, or proximal thereof. At the proximal end of handle 24 is electrical connector 32 for connecting tip electrode 20, band electrodes 22 and the thermocouple to RF power, mapping, and/or temperature measuring equipment. Tip section 16, as illustrated in FIG. 3, is flexible and laterally deflectable into various configurations using shapable handle 24.

Referring now to FIGS. 2, 3 and 5, shaft 10 comprises an outer jacket 34, which may be nylon, urethane or other plastic. As shown in FIGS. 3 and 5, outer jacket 34 surrounds stiffener 36, which usually comprises a stainless steel braid or coil.

The stiffener 36 is disposed about a base layer 38, which preferably comprises a tube of polyimide or other relatively stiff, high durometer material. The stiffness and torqueability characteristics of the shaft can be varied by varying the type of material used for outer jacket 34, stiffener 36 and base layer 38, as well as by using different geometry's for the stiffener 38. For example, the stiffener 36 could be a braid or a coil, where the number of filaments, shape of filaments coiling or weaving pattern, number of turns, and the like, can be varied individually or in combination to provide a desired stiffness. Preferably, the polyimide tube of base layer 38 has a thickness in the range from 0.002 in to 0.005 in. Outer jacket 34, stiffener 36 and base layer 38 define a central lumen 40 extending the length of shaft 10. Disposed in central lumen 40 are a core wire 42, pull wires 44, electrode wires 46, and thermocouple wires 48.

Referring now to FIGS. 2, 4 and 5, tip section 16 comprises tubing 50 of a low durometer flexible plastic, such as Pebax™, silicone rubber, or other resilient material.

Preferably, tip section 16 has a durometer in the range of 30A to 60D. Tubing 50 usually has at least four lumens extending its length in parallel to its longitudinal axis, a central lumen 54 and at least three radially offset lumens 56 (with four being illustrated). Core wire 42 extends through central lumen 54, along with electrode wires 46 and thermocouple wires 48. Pull wires 44 extend from the central lumen of shaft 10 to the radially offset lumens 56 of tip section 16. A spring tube 58 is also disposed in central lumen 54 of tip section 16, the spring tube 59 fitting snugly against the walls of inner lumen 54 and having a hollow center through which core wire 42, electrode wires 46 and thermocouple wires 48 extend. Spring tube 58 usually comprises a polyimide tube which provides lateral and torsional stiffness as well as kink-resistance to tip section 16. The spring tube 58 could also be a braided or coded structure, or a composite of multiple layers.

Referring now particularly to FIG. 5, tip section 16 is fixed to shaft 10 at butt joint 18, preferably by heat welding. Central lumen 54 of tip segment 16 is of smaller diameter than central lumen 40 of shaft 10, with spring tube 58 extending a distance, typically about 0.5 in., into the central lumen 40 of shaft 10. Such extension serves to limit kinking at or near butt joint 18 when tip section 16 is deflected. A proximal end 60 of the spring tube 59 will extend into central lumen 40, thereby enhancing the stiffness at the transition between the tip section 16 and the remainder of the shaft 10.

Core wire 42, electrode wires 46 and thermocouple wires 48 extend from central lumen 40 of shaft 10 into central lumen 54 of tip section 16 through the center of spring tube 58. At the distal end of tip section 16, spring tube 59 emerges from central lumen 54 into an aperture 64 within tip electrode 20. RF power wire 66 (one of electrode wires 46) is coupled to tip electrode 20. Thermocouple wires 48 terminate in a thermocouple 68 disposed within aperture 64. Preferably, aperture 64 is filled with high temperature adhesive to maintain thermocouple 68 in position. Electrode band wires 70 exit central lumen 54 within spring tube 58 and couple to band electrodes 22. Core wire 42 extends through central lumen 54 into aperture 64 of tip electrode 20.

An electrically and thermally insulating anchor plate 72 is bonded to distal end 74 of tubing 50, and tip electrode 20 is bonded to the distal side of anchor plate 72.

Anchor plate 72 has a central passage co-axially aligned with central lumen 54 of tip section 16, and four radially offset apertures 76 through which pull wires 44 pass. Referring again to FIG. 5, pull wires 44 terminate in anchors 80, which usually comprise steel balls formed on or welded to ends of pull wires 44. The anchors 80 are of larger diameter than apertures 76, providing a strong, pivotal connection between pull wires 44 and the distal end of tip section 16. Anchor plate 72 protects the catheter body 10 from thermal damage during ablation, allowing for many RF applications without catheter body degradation. It also provides a strong component to which the pull wires 44 can be attached, without reliance on adhesive, and electrically insulates the pull wires 44 from tip electrode 20, preventing the RF current from traveling back up the catheter to the handle assembly. The anchor plate 72 may be formed from any polymeric or ceramic material having the necessary mechanical strength and electrical and thermal insulating properties, e.g., polyether ether ketone, available from ICI Americas, Inc., Wilimington, Del., under the trade name Victrex.

FIGS. 6 and 7 show the tip electrode 20 in a cross-section partial view and an end view, respectively to highlight the slip resistant, field focusing exterior contour shape in accordance with the first embodiment of the invention. Distal tip electrode 20 is formed of a generally cylindrical, electrically conductive, electrode body having a hemispheric end and a tubular side wall 96 at the distal end of the catheter body 10. Distal tip electrode 20 is provided with an axial depression, e.g. a bore 86 axially drilled or otherwise formed into the hemispheric end, and a plurality, e.g., two, circular, V-shaped grooves 82 and 84 between the axial bore 86 and side wall 96. Annular grooves 82 and 84 and bore 86 divide the outer-most surface of electrode 20 into two annular areas or ridges 92 and 94. Axial exterior bore 86 and groove 82 define an angle 88, which may be about 60–70 degrees. Axial exterior bore 86 and groove 84 define an angle 90 which, may be 30–40 degrees. Grooves 28 and 30 are cut to a depth of about 0.010±0.002 inches at an angle 98 which may be about 60±15 degrees. The outer diameter of the tip electrode side wall 96 is preferably 7 French or 0.091±0.002 inches. The length of outer side wall 96 is preferably 0.160±0.005 inches to provide sufficient surface area to distribute the RF ablation energy to the endocardium.

The edges defined by the grooves and annular areas or rings of electrode 20 depicted in FIGS. 5–7 provide areas of small radius of curvature, which are believed to provide localized increases in current density. Current distribution is directed axially and distally of the distal tip electrode focused into the myocardium without requiring physical penetration into it by the distal tip electrode 20. In addition, the edges of the axial exterior bore 86 and the grooves 82, 84 provide edges that roughen the exterior surface contour of the distal tip electrode 20 and cause it to be slip resistant when placed as shown in FIG. 1.

Precise adherence to the dimensions given above is not believed necessary to practice the invention. However, it is believed to be desirable that the edges defined by the grooves and annular areas display a small radius of curvature. Arranging the annular grooves generally perpendicular to the direction in which force is asserted to hold the distal tip electrode in position against the endocardium is also believed to be beneficial.

The ridges formed of the electrode body remaining after the grooves 82, 84 are cut also should provide enhanced cooling of the electrode by the blood flowing during beating of the heart. In the ablation procedure, cooling may take place as the electrode tip is being repositioned to a new site. It may also be desirable to include depressions, e.g. longitudinal slots, dimples or an additional annular groove, cut into the side wall 96 proximal to annular groove 82 to enhance cooling. In such a case, the width of side wall 96 would be increased to make up for the lost mass.

Figure 8:
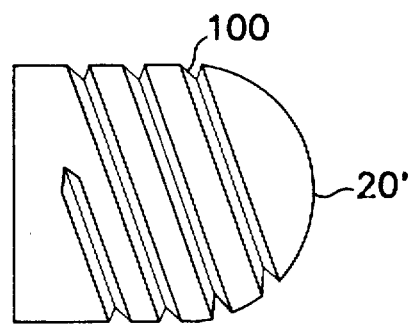
FIG. 8 is an enlarged, side cross-section view of the catheter body and distal tip electrode shaped in accordance with a second preferred embodiment of the invention.

FIG. 8 is an enlarged side view illustrating a second preferred embodiment of the exterior contour wherein the distal tip electrode 20' is formed of a generally cylindrical, electrically conductive, electrode body having a hemispheric end and a tubular side wall 96 attached at the distal end of the catheter body in the manner shown in FIG. 5. The exterior contour is formed by one or more spiral groove 100 cut in the hemispheric end and extending proximally along the side wall 96, with or without an axially disposed bore 86 depicted in FIGS. 5–7.

Figure 9:
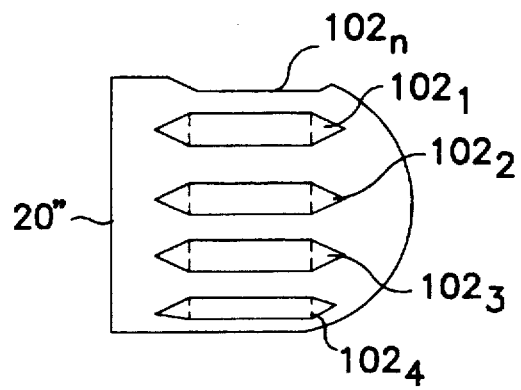

In a third preferred embodiment of the exterior contour depicted in FIG. 9, the exterior contour may comprise one or more longitudinal or particularly shaped grooves $102_1$–$102_n$ extending along the side wall 96 of the distal tip electrode 20". The elongated grooves of this embodiment may be combined with the embodiment of FIGS. 5–7 with or without the distal bore 86.

Figure 10:
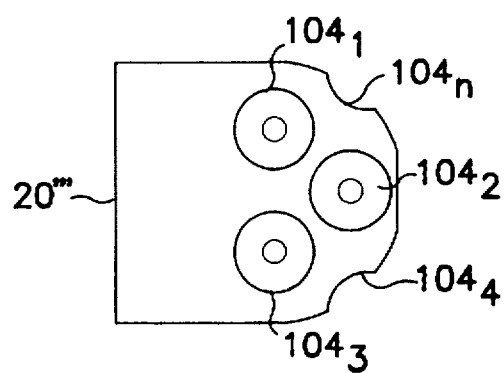
FIG. 10 is a side cross-section view of a catheter body distal tip section having a distal tip electrode shaped in accordance with a fourth preferred embodiment of the invention.

In a further preferred embodiment, the exterior contour of the distal tip electrode 20''' may take the shape of a depressions or dimples $104_1$–$104_n$ as shown in FIG. 10. The surface irregularities to reduce slippage and to provide the other benefits of the invention may therefore take a wide variety of forms.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

I claim:

1. A method of ablation comprising:

advancing a catheter carrying a distal tip electrode having a distal facing surface provided with at least one depression formed therein having edges with a small radius of curvature to prevent slippage of the distal facing surface, to a desired location within the body and from a proximal end of the catheter and manipulating the distal facing surface of the tip electrode into contact with body tissue at the desired location; and ablating tissue at the desired location by application of electrical energy to the tip electrode while the distal facing surface is located in contact with tissue at the desired location.

2. A method according to claim 1 wherein said advancing step comprises advancing a catheter having a tip electrode with a hemispherical distal facing surface.

3. A method according to claims 1 or 2 wherein said advancing step comprises advancing a catheter having a tip electrode with a distal facing surface at least one annular groove formed therein.

4. A method according to claims 1 or 2 wherein said advancing step comprises advancing a catheter having a tip electrode with a distal facing surface having at least one spiral groove formed therein.

5. A method according to claims 1 or 2 wherein said advancing step comprises advancing a catheter having a tip electrode with a distal facing surface having multiple depressions formed therein.

6. A method according to claims 1 or 2 wherein said manipulating step comprises deflecting a distal portion of the catheter.

7. A method according to claims 1 or 2 wherein said advancing step comprises advancing a catheter having a handle at a proximal end thereof comprising means for deflecting a distal portion of the catheter and wherein said manipulating step comprises deflecting a distal portion of the catheter using said deflecting means on said handle.

8. A method according to claims 1 or 2 wherein said applying step comprises applying RF electrical energy.

* * * * *